US007312324B2

(12) United States Patent
Souza et al.

(10) Patent No.: US 7,312,324 B2
(45) Date of Patent: Dec. 25, 2007

(54) REGULATORY ELEMENTS FOR DELIVERY TO THE LIVER

(75) Inventors: David W. Souza, Waltham, MA (US); Donna Armentano, Belmont, MA (US); Samuel C. Wadsworth, Shrewsbury, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 10/139,763

(22) Filed: May 6, 2002

(65) Prior Publication Data

US 2003/0017139 A1    Jan. 23, 2003

Related U.S. Application Data

(63) Continuation of application No. 09/712,775, filed on Nov. 14, 2000, now abandoned.

(51) Int. Cl.
C07H 21/04    (2006.01)
C07H 21/02    (2006.01)
A01N 63/00    (2006.01)
A01N 65/00    (2006.01)
A01N 43/04    (2006.01)
A01N 31/70    (2006.01)

(52) U.S. Cl. .................. 536/24.1; 514/44; 424/93.1; 536/23.1

(58) Field of Classification Search ............ 536/24.1; 514/44; 435/320.1, 325; 424/93.1
See application file for complete search history.

(56) References Cited

U.S. PATENT DOCUMENTS 5,965,541 A * 10/1999 Wickham et al. ............ 514/44
2002/0155095 A1* 10/2002 Nagabhushan et al. ..... 424/93.1
2003/0224508 A1* 12/2003 Ill et al. ................ 435/320.1

FOREIGN PATENT DOCUMENTS

| DE | 4339922 | 10/1994 |
|---|---|---|
| DE | 4407859 | 3/1995 |
| EP | 0589851 | 3/1994 |
| WO | WO 95/11308 | 4/1995 |
| WO | WO 97/04117 | 2/1997 |
| WO | WO 98/09524 | 3/1998 |
| WO | WO 99/29848 | 6/1999 |
| WO | 99/36557 | * 7/1999 |
| WO | WO 99/36557 | 7/1999 |

OTHER PUBLICATIONS

Rouet. Nucleic Acids Research 1995, vol. 23, No. 3, p. 395-404.*
Okuyama et al. (Human Gene Therapy, 7: 637-645, Mar. 1996.*
Kay et al. Human Gene Therapy 3:641-647, 1992.*
Greenberg et al. Proc. Natl. Acad. Sci. USA 92:12347-12351.*
Sabourin et al. The Journal of Biological Chemistry 271:3469-3473, 1996.*

Darzan et al (Journal of Surgical Research 59:299-304, 1995.*
Allan, Charles M. et al., Two Hepatic Enhancers, HCR.1 and HCR.2, Coordinate the Liver Expression of the Entire Human Apolipoprotein E/C-I/C-IV/C-II Gene Cluster, The Journal of Biological Chemistry, vol. 272, No. 46, Nov. 14, 1997, pp. 29113-29119; by the American Society for Biochemistry and Molecular Biology, Inc.
Armentano, Donna et al., Effect of the E4 Region on the Persistence of Transgene Expression from Adenovirus Vectors, Journal of Virology, vol. 71, No. 3, Mar. 1997, pp. 2408-2416; American Society for Microbiology.
Armentano, Donna et al., E4ORF3 Requirement for Achieving Long-Term Transgene Expression from the Cytomegalovirus Promoter in Adenovirus Vectors, Journal of Virology, Aug. 1999, vol. 73, No. 8, pp. 7031-7034; American Society for Microbiology.
Bell, Adam C. et al., The Protein CTCF Is Required for the Enhancer Blocking Activity of Vertebrate Insulators, Cell, vol. 98, Aug. 6, 1999, pp. 387-396; Cell Press.
Berkner, K.L., Expression of Heterologous Sequences in Adenoviral Vectors, Current Topics in Microbiology and Immunology, vol. 158, pp. 39-66; Springer-Verlag Berlin Heidleberg 1992.
Brough, Douglas E. et al., Activation of Transgene Expression by Early Region 4 is Responsible for a High Level of Persistent Transgene Expression from Adenovirus Vectors In Vivo, Journal of Virology, Dec. 1997, vol. 71, No. 12, pp. 9206-9213; American Society for Microbiology.
Chow, Billy, K.C. et al., Characterization of a Novel Liver-Specific Enhancer in the Human Prothrombin Gene, The Journal of Biological Chemistry, vol. 266, No. 28, Oct. 5, 1991, pp. 18927-18933; The American Society for Biochemistry and Molecular Biiology, Inc.
Ciliberto, Gennaro et al., Cell-Specific Expression of a Transfected Human alpha 1-Antitrypsin Gene, Cell, vol. 41, Jun. 1985, pp. 531-540; MIT.
Connelly, Sheila et al., Sustained Phenotypic Correction of Murine Hemophilia A by In Vivo Gene Therapy, Blood, vol. 91, No. 9, May 1, 1998, pp. 3273-3281; The American Society of Hematology.
Crystal, Ronald G. et al., Administration of an Adenovirus Containing the Human CFTR cDNA to the Respiratory Tract of Individuals with Cystic Fibrosis, Nature Genetics, vol. 8, Sep. 1994, pp. 42-61.

(Continued)

*Primary Examiner*—Joseph Woitach
*Assistant Examiner*—Robert M. Kelly

(57) ABSTRACT

The invention is directed to novel combinations of liver specific enhancers and promoter elements for achieving persistent transgene expression in the liver. The liver specific enhancer elements may be derived from either the human serum albumin, prothrombin, α-1microglobulin or aldolase genes in single copies or in multimerized form linked to elements derived from the cytomegalovirus intermediate early (CMV), α-1-antitrypsin or albumin promoters. In a preferred embodiment of the invention, an adenoviral vector comprising a liver specific enhancer/promoter combination operably linked to a transgene is administered to recipient cells. In other embodiments of the invention, adeno-associated viral vectors, retroviral vectors, lentiviral vectors or a plasmid comprising the liver specific enhancer/promoter combination linked to a transgene is administered to recipient cells. Also within the scope of the invention are promoter elements derived from the human prothrombin gene and the β-fibrinogen gene.

11 Claims, 9 Drawing Sheets

OTHER PUBLICATIONS

Dedieu, Jean-Francois et al., Long-Term Gene Delivery into the Livers of Immunocompetent Mice with E1/E4-Defective Adenoviruses, Journal of Virology, Jun. 1997, vol. 71, No. 6, pp. 4626-4637; American Society for Microbiology.

Donello, John E. et al., Woodchuck Hepatitis Virus Contains a Tripartite Posttranscriptional Regulatory Element, Journal of Virology, Jun. 1998, vol. 72, No. 6, pp. 5085-5092; American Society for Microbiology.

Frain, Monique et al., Binding of a Liver-Specific Factor to the Human Albumin Gene Promoter and Enhancer, Molecular and Cellular Biology, Mar. 1990, vol. 10, No. 3, pp. 991-999; American Society for Microbiology.

Gregori, Claudine et al., Characterization of the Aldolase B Intronic Enhancer, The Journal of Biological Chemistry, vol. 273, No. 39, 1998, pp. 25237-25243; The American Society for Biochemistry and Molecular Biology, Inc.

Guo, ZS et al., Evaluation of Promoter Strength for Hepatic Gene Expression In Vivo Following Adenovirus-Mediated Gene Transfer, Gene Therapy (1996), vol. 3, pp. 802-810; Stockton Press.

Hafenrichter, Daniel G. et al., Liver-Directed Gene Therapy: Evaluation of Liver Specific Promoter Elements, Journal of Surgical Research, vol. 56, pp. 510-517 (1994); Academic Press, Inc.

Hafenrichter, Daniel G. et al., Quantitative Evaluation of Liver-Specific Promoters from Retroviral Vectors after in Vivo Transduction of Hepatocytes, Blood, vol. 84, No. 10, Nov. 15, 1994, pp. 3394-3404; The American Society of Hematology.

Hayashi, Yoshitake et al., Identification and Characterization of Two Enhancers of the Human Albumin Gene, The Journal of Biological Chemistry, vol. 267, No. 21, Jul. 25, 1992, pp. 14580-14585; The American Society for Biochemistry and Molecular Biology.

Holcik, Martin et al., Four Highly Stable Eukaryotic mRNAs-Assemble 3' Untranslated Region RNA-Protein Complexes Sharing Cis and Trans Components, Proc. Natl. Acad. Sci., USA, vol. 94, pp. 2410-2414, Mar. 1997; Developmental Biology.

Huber, P. et al., Human Beta-Fibrinogen Gene Expression, The Journal of Biological Chemistry, vol. 265, No. 10, Apr. 5, 1990, pp. 5695-5701; The American Society for Biochemistry and Molecular Biology, Inc.

Ill, Charles R. et al., Optimization of the Human Factor VIII Complementary DNA Expression Plasmid for Gene Therapy of Hemophilia A, Blood Coagulation and Fibrinolysis, vol. 8, Suppl. 2, (1997), pp. S23-S30; Rapid Science Publishers.

Jolly, Douglas, Cancer Gene Therapy, vol. 1, No. 1, 1994, pp. 51-64; Nature Publishing Group.

Morral, Nurla et al., High Doses of a Helper-Dependent Adanoviral Vector Yield Supraphysiological Levels of Alpha 1-Antitrypsin with Negligible Toxicity, Human Gene Therapy, vol. 9, Dec. 10, 1998, pp. 2709-2716; Mary Ann Liebert, Inc.

Nakai, Hiroyuki et al., Adeno-Associated Viral Vector-Mediated Gene Transfer of Human Blood Coagulation Factor IX into Mouse Liver, Blood, vol. 91, No. 12, Jun. 15, 1998, pp. 4600-4607; The American Society of Hematology.

Okuyama, Torayuki et al., Liver-Directed Gene Therapy: A Retroviral Vector with a Complete LTR and the ApoE Enhancer-alpha 1-Antitrypsin Promoter Dramatically Increases Expression of Human alpha 1-Antitrypsin In Vivo, Human Gene Therapy, vol. 7, Mar. 20, 1996, pp. 637-645; Mary Ann Liebert, Inc.

Ponder, Katherine Parker et al., Evaluation of Relative Promoter Strength in Primary Hepatocytes Using Optimized Lipofection, Human Gene Therapy, vol. 2, (1991), pp. 41-52; Mary Ann Liebert, Inc., Publishers.

Rettinger, Steven D. et al., Liver-Directed Gene Therapy: Quantitative Evaluation of Promoter Elements by Using In Vivo Retroviral Transduction, Proc. Natl. Acad. Sci. USA, vol. 91, Feb. 1994, pp. 1460-1464; Genetics.

Rich, Devra P. et al., Development and Analysis of Recombinant Adenoviruses for Gene Therapy of Cystic Fibrosis, Human Gene Therapy, vol. 4, (1993), pp. 461-476; Mary Ann Liebert, Inc., Publishers.

Rouet, Philippe et al., A Potent Enhancer Made of Clustered Liver-Specific Elements in the Transcription Control Sequences of Human Alpha 1-Microglobulin/Bikurin Gene, The Journal of Biological Chemistry, vol. 267, No. 29, Oct. 15, 1992, pp. 20765-20773; The American Society for Biochemistry and Molecular Biology, Inc.

Rouet, Philippe et al., Hierarchy and Positive/Negative Interplays of the Hepatocyte Nuclear Factors HNF-1, -3 and -4 in the Liver-Specific Enhancer for the Human Alpha-1-Microglobulin/Bikunin Precursor, Nucleic Acids Research, vol. 23, No. 3, (1995), pp. 395-404; Oxford University Press.

Rouet, Philippe et al., An Array of Binding Sites for Hepatocyte Nuclear Factor 4 of High and Low Affinities Modulates the Liver-Specific Enhancer for the Human Alpha 1-Microglobulin/Bikunin Precursor, Biochem. J., vol. 334, (1998), pp. 577-584; Portland Press.

Sandig, V. et al., HBV-Derived Promoters Direct Liver-Specific Expression of an Adenovirally Transduced LDL Receptor Gene, Gene Therapy, vol. 3, (1996) pp. 1002-1009; Stockton Press.

Schiedner, Gudrun et al., Genomic DNA Transfer with a High-Capacity Adenovirus Vector Results in Improved In Vivo Gene Expression and Decreased Toxicity, Nature Genetics, vol. 18, Feb. 1998, pp. 180-183.

Stratford-Perricaudet, Leslie D. et al., Evaluation of the Transfer and Expression in Mice of an Enzyme-Encoding Gene Using a Human Adenovirus Vector, Human Gene Therapy, vol. 1, (1990), pp. 241-256; Mary Ann Liebert, Inc., Publishers.

Wang, O. et al., Persistent Transgene Expression in Mouse Liver Following In Vivo Gene Transfer with a Delta E1/Delta E4 Adenovirus Vector, Gene Therapy, vol. 4, (1997), pp. 393-400; Stockton Press.

Wang, Xiaoming et al., Detection and Characterization of a 3' Untranslated Region Ribonucleoprotein Complex Associated with Human Alpha-Globin mRNA Stability, Molecular and Cellular Biology, Mar. 1995, vol. 15, No. 3, pp. 1769-1777; American Society for Microbiology.

Xiao, Weidong et al., Adeno-Associated Virus as a Vector for Liver-Directed Gene Therapy, Journal of Virology, Dec. 1998, vol. 72, No. 12, pp. 10222-10226; American Society for Microbiology.

Zabner, Joseph et al., Adenovirus-Mediated Gene Transfer Transiently Corrects the Chloride Transport Defect in Nasal Epithelia of Patients with Cystic Fibrosis, Cell, vol. 75, Oct. 22, 1993, pp. 207-216; Cell Press.

Zabner, Joseph et al., Safety and Efficacy of Repetitive Adenovirus-Mediated Transfer of CFTR cDNA to Airway Epithella of Primates and Cotton Rats, Nature Genetics, vol. 6, Jan. 1994, pp. 75-83.

Zufferey, Romain et al., Woodchuck Hepatitis Virus Post-transcriptional Regulatory Element Enhances Expression of Transgenes Delivered by Retroviral Vectors, Journal of Virology, Apr. 1999, vol. 73, No. 4, pp. 2886-2892; American Society for Microbiology.

* cited by examiner

GRAPHIC REPRESENTATION OF THE PROMOTERS INVESTIGATED AND SOME OF THEIR TRANSCRIPTION FACTOR BINDING SITES

A. (HSA) HUMAN SERUM ALBUMIN ENHANCER/ (mCMV = ΔCMV) PROMOTER
(HSA) HUMAN SERUM ALBUMIN ENHANCER/ HUMAN SERUM ALBUMIN PROMOTER

B. (HPrT) PROTHROMBIN ENHANCER/ (mCMV = ΔCMV) PROMOTER

C. (A1MB) α-1-MICROGLOBULIN ENHANCER/ (mCMV = ΔCMV) PROMOTER

D. (HPrT) PROTHROMBIN ENHANCER/ (A1AT) α-1-ANTITRYPSIN PROMOTER

E. (A1MB) α-1-MICROGLOBULIN ENHANCER/ (A1AT) α-1-ANTITRYPSIN PROMOTER

AGAL EXPRESSION DATA IN HEP3 B CELLS 9-20-99

1. SV2 CMV HI AGAL
2. SV2 mCMV HI AGAL
3. SV2 1.7(5) 6(1) mCMV HI AGAL
4. SV2 HPrT(2) mCMV HI AGAL
5. SV2 A1MB(8) mCMV HI AGAL
6. SV2 A1AT HI AGAL
7. SV2 HPrT(2) A1AT HI AGAL
8. SV2 HPrT(2) ALD(1)A1AT HI AGAL
9. SV2 A1MB(2) A1AT HI AGAL
10. AdTBG
11. AdA1BPR

REGULATORY ELEMENTS FOR DELIVERY TO THE LIVER

FIELD OF THE INVENTION

This invention relates to nucleic acid delivery vehicle constructs that have an enhanced capability of expression in target cells, namely to hepatocytes and other liver cells.

BACKGROUND OF THE INVENTION

The ability to deliver nucleic acids carried by delivery vehicles, e.g., recombinant viruses (adenovirus, adeno-associated virus, herpesvirus, retrovirus) which are used with nucleic acid molecules, such as a plasmid, comprising a transgene, to transfect a target cell; molecular conjugate vectors; and modified viral vectors are important for the potential treatment of genetic diseases through gene delivery.

Adenovirus is a non-enveloped, nuclear DNA virus with a genome of about 36 kb. See generally, Horwitz, M. S., "Adenoviridae and Their Replication," in *Virology*, 2nd edition, Fields et al., eds., Raven Press, New York, 1990. Recombinant (adenovirus dodecahedron and recombinant adenovirus conglomerates) to specific cell types is useful for various applications in oncology, developmental biology and gene therapy. Adenoviruses have advantages for use as expression systems for nucleic acid molecules coding for, inter alia, proteins, ribozymes, RNAs, antisense RNA that are foreign to the adenovirus carrier (i.e. a transgene), including tropism for both dividing and non-dividing cells, minimal pathogenic potential, ability to replicate to high titer for preparation of vector stocks, and the potential to carry large inserts. See Berkner, K. L., 1992, *Curr. Top. Micro Immunol*, 158:39-66; Jolly D., 1994, *Cancer Gene Therapy*, 1:51-64.

Adenoviruses have a natural tropism for respiratory tract cells, which has made them attractive vectors for use in delivery of genes to respiratory tract cells. For example, adenovirus vectors have been and are being designed for use in the treatment of certain diseases, such as cystic fibrosis (CF): the most common autosomal recessive disease in Caucasians. In CF, mutations in the cystic fibrosis transmembrane conductance regulator (CFTR) gene disturb cAMP-regulated chloride channel function, resulting in pulmonary dysfunction. The gene mutations have been found to encode altered CFTR proteins which cannot be translocated to the cell membrane for proper functioning. The CFTR gene has been introduced into adenovirus vectors to treat CF in several animal models and human patients. Particularly, studies have shown that adenovirus vectors are fully capable of delivering CFTR to airway epithelia of CF patients, as well as airway epithelia of cotton rats and primates. See e.g., Zabner et al., 1994, *Nature Genetics*, 6:75-83; Rich et al., 1993, *Human Gene Therapy*, 4:461-476; Zabner et al., 1993, *Cell*, 75:207-216; Zabner et al., 1994, *Nature Genetics* 6:75-83; Crystal et al., 1004, *Nature Genetics*, 8:42-51; Rich et al., 1993, *Human Gene Therapy*, 4:461-476.

However, it would be useful to alter the genome of adenovirus, to allow it to be used to deliver a nucleic acid molecule that would be enhanced for expression in the liver, particularly in hepatocytes.

It would be useful to mediate expression of the transgene carried by the adenoviral vector through the use of one or more specialized regulatory elements. In this way the expression of transgene within desired cells can be enhanced and the adenovirus effects can be targeted to certain cells or tissues within an organism.

Like adenoviruses, retroviruses have also been used for delivery of transgenes to target cells. As set forth above, a transgene is a nucleic acid molecule that codes for, inter alia, a protein, RNA, ribozyme, antisense RNA not produced by the virus. Retrovirus virions range in diameter from 80 to 130 nm and are made up of a protein capsid that is lipid encapsulated. The viral genome is encased within the capsid along with the proteins integrase and reverse transcriptase. The retrovirus genome consists of two RNA strands. After the virus enters the cells, the reverse transcriptase synthesizes viral DNA using the viral RNA as its template. The cellular machinery then synthesizes the complementary DNA which is then circularized and inserted into the host genome. Following insertion, the viral RNA genome is transcribed and viral replication is completed.

Examples of retroviruses include Moloney murine leukemia virus (Mo-MuLV), HTLV and HIV retroviruses. Mo-MuLV vectors are most commonly used and are produced simply by replacing viral genes required for replication with the desired transgenes to be transferred. The genome in retroviral vectors contains a long terminal repeat sequence (LTR) at each end with the desired transgene or transgenes in between. The most commonly used system for generating retroviral vectors consists of two parts, the retroviral vector and the packaging cell line.

Retroviruses are typically classified by their host range. For example, ecotropic viruses are viruses which bind receptors unique to mice and are only able to replicate within the murine species. Xenotropic viruses bind receptors found on all cells in most species except those of mice. Polytropic and amphotropic viruses bind different receptors found in both murine and nonmurine species. The host range is determined primarily by the binding interaction between viral envelope glycoproteins and specific proteins on the host cell surface that act as viral receptors. For example, in murine cells, an amino acid transporter serves as the receptor for the envelope glycoprotein gp70 of ecotropic Moloney murine leukemia virus (Mo-MuLV). The receptor for the amphotropic MoMuLV has recently been cloned and shows homology to a phosphate transporter. There are six known receptors for retroviruses: CD4 (for HIV); CAT (for MLV-E (ecotropic Murine leukemic virus E); RAM1/GLVR2 (for murine leukemic virus-A (MLV-A)); GLVRI (for Gibbon Ape leukemia virus (GALV) and Feline leukemia virus B (FeLV-B). RAM1 and GLVR1 receptors are broadly expressed in human tissues.

Retrovirus packaging cell lines provide all the viral proteins required for capsid production and the virion maturation of the vector, i.e., the gag, pol and env genes. For the MMLV vectors, it is the packaging cell line that determines whether the vector is ecotropic, xenotropic or amphotropic. The choice of the packaging cell line determines the cells that will be targeted. Thus, the usefulness of retroviruses for gene transfer is limited by the fact that they are receptor specific.

However, retroviruses are useful for gene delivery systems because they have a high infection efficiency and the retroviral nucleic acid (after reverse transcription) integrates into the host genome resulting in sustained expression of the transgenes carried by the vector. However, typical retroviral vectors are limited in that they require dividing cells for infectivity. Furthermore, in vivo delivery of these vectors is poor and is effective only when infecting helper cell lines.

Thus, it would be useful to have a system for increasing the efficiency of retroviral infection.

Certain situations exist where it would be useful to modify the expression of transgenes carried by viruses. For example, tissue-specific expression of the transgene in targeted cells might increase the efficiency of infection, and consequently, a lower volume of virus may be effective in the body. It would be useful to have a method of up-regulating the expression of the transgene in a tissue-specific manner.

One method for targeting specific cell populations to express a protein of interest is to use heterologous regulatory elements that are specifically expressed in the desired target tissue or cell populations. This may be achieved through the use of combinations of tissue-specific enhancers, promoters and/or other regulatory elements. The regulatory elements may be constitutive or inducible, such that they are regulated by the absence or presence of other DNA sequences, proteins or other elements or environmental factors. Where the transgene of interest is a cytotoxic gene, leaky expression would be highly undesirable.

SUMMARY OF THE INVENTION

Accordingly, the present invention provides improved regulatory elements that are useful for targeting transgene expression to the liver. In preferred embodiments, the regulatory elements comprise combinations of promoter and enhancer elements that are able to direct transgene expression preferentially in liver. In particular embodiments, the regulatory elements are used in recombinant vectors, such as such as nonviral plasmid based vectors or such as viral vectors, including adenovirus, adeno-associated virus, retrovirus and lentivirus, including the human immunodeficiency [HIV] virus. In other embodiments, the invention comprises recombinant vectors useful for transgene expression, particularly for high and sustained expression in the liver, such as viral vectors. The vectors comprise combinations of a constitutive or high-expressing promoter and one or more liver-specific enhancer elements.

Thus, the present invention comprises recombinant transgenes comprising strong constitutive promoters and one or more liver-specific enhancer elements. The transgenes may be used in recombinant vectors, such as recombinant viral vectors, for targeting expression of the associated coding DNA sequences preferentially in liver. In preferred embodiments, the strong constitutive promoter is selected from the group comprising a CMV promoter, a truncated CMV promoter, human serum albumin promoter and α-1-antitrypsin promoter. In other preferred embodiments, the promoter is a truncated CMV promoter from which binding sites for known transcriptional repressors have been deleted.

In other embodiments, the liver-specific enhancer elements are selected from the group consisting of human serum albumin [HSA] enhancers, human prothrombin [HPrT] enhancers, α-1microglobulin enhancers and intronic aldolase enhancers. One or more of these liver-specific enhancer elements may be used in combination with the promoter. In one preferred embodiment of the invention, one or more HSA enhancers are used in combination with a promoter selected from the group consisting of a CMV promoter or an HSA promoter. In another preferred embodiment, one or more enhancer elements selected from the group consisting of human prothrombin (HPrT) enhancers and α-1microglobulin (A1MB) enhancers are used in combination with the CMV promoter. In yet another preferred embodiment, the enhancer elements are selected from the group consisting of HPrT enhancers and A1MB enhancers, and are used in combination with the α-1-antitrypsin promoter.

The preferred embodiments of the present invention are recombinant viral vectors, particularly adenoviral vectors. In the preferred embodiments, the coding DNA sequence may encode a therapeutic protein that is most effective when delivered to the liver. The adenoviral vectors may comprise, in addition to the promoters and enhancers of the present invention, one or more adenoviral genes in order to support the efficient expression of the coding DNA sequence.

Expression levels detected on day one were comparable in mice that received either plasmid indicating that the hybrid promoter could yield expression levels that approximate that from the CMV promoter. However, expression from the CMV promoter was transient and plummeted to undetectable by day seven whereas expression from the hybrid promoter persisted to day 14 (the last time point of this experiment). This suggests that this hybrid promoter is a better choice for achieving long-term transgene expression in the liver.

Figure 9:
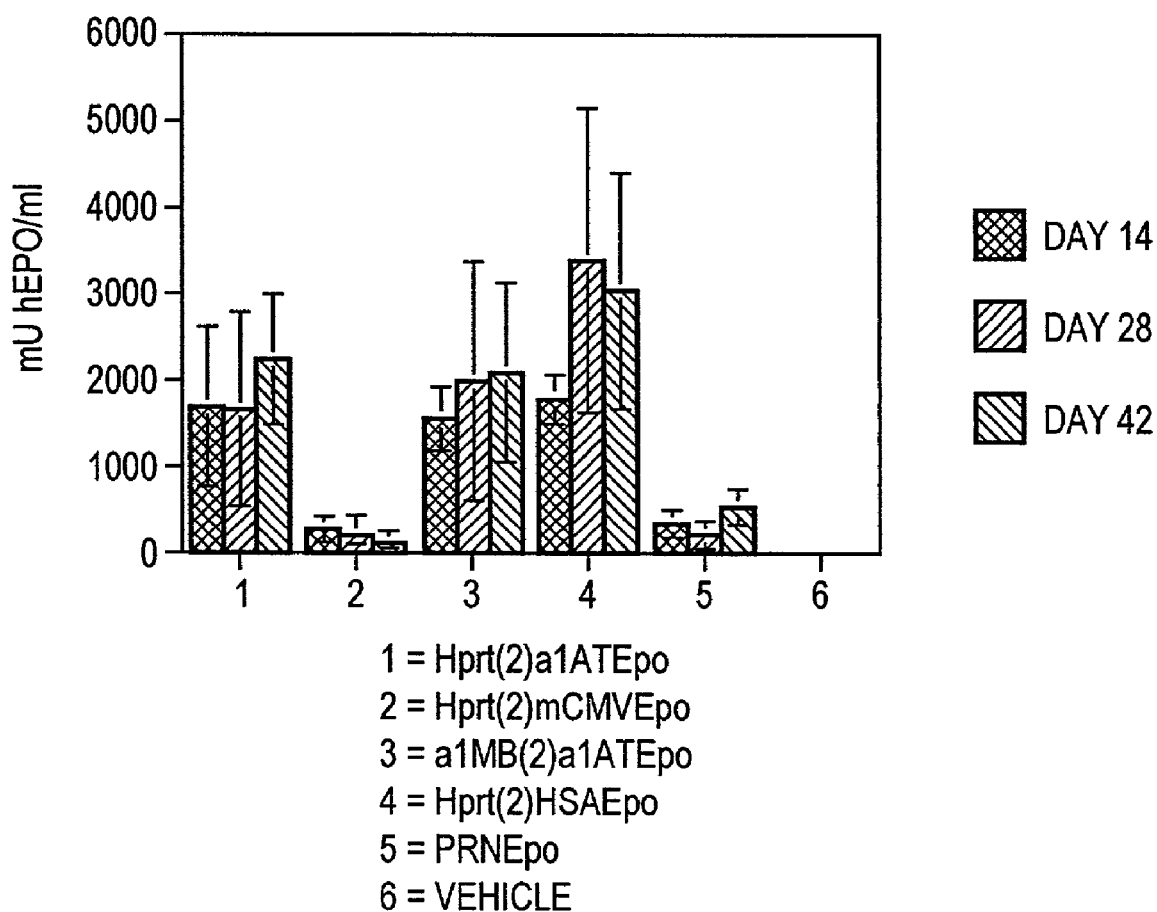

FIG. 9 demonstrates the AAV mediated expression of recombinant human erythropoietin [EPO] in mice. From promoter studies in cultured Hep3B cells, several enhancer/promoter combinations were identified as promising candidates for achieving long-term expression in the liver. From this panel of combinations, several were cloned into AAV vectors to test their ability to drive expression of recombinant human EPO. 1×10e11 particles of each AAV vector was administered to NCR nude mice by portal vein injection. On days 14, 28 and 42 post-injection, the mice were bled retro-orbitally and EPO levels were determined by an ELISA specific for human EPO. All promoters shown in the above figure gave rise to persistent expression out to day 42. However from this analysis, three enhancer/promoter combinations emerge as being the most promising for yielding high persistent levels of expression. Two copies of the hprt enhancer linked to either the α-1AT or HSA promoters and two copies of the α-1-microglobulin enhancer linked to the α-1-AT promoter yielded expression ranging from 1500 to 3000 mU EPO/ml or from 300 μg to 600 μg protein/ml.

DETAILED DESCRIPTION OF THE INVENTION

The delivery of genes to the liver for therapeutic purposes has been explored extensively. This includes investigation aimed at correction of genetic diseases of the liver as well as systemic diseases that might be corrected by using the liver as a depot for therapeutic protein production. For this gene therapy approach to be feasible, expression of the therapeutic gene must be long-lived and approach appropriate levels. In several reports, the use of a variety of viral, non-viral, and liver specific promoters as well as various enhancer/promoter combinations has been explored in the context of adenoviral, AAV, retroviral and plasmid-based vectors for gene expression in cultured cells and in vivo. In many of these examples transgene expression was transient and/or not sufficient to achieve therapeutic benefit. In the context of adenoviral vectors, the CMV promoter and RSV promoter direct high levels of transgene expression however the longevity of expression is dependent upon retention of the adenoviral E4 region in the vector. The development of an enhancer/promoter combination that can direct sustained and appropriate levels of transgene expression in the context of a variety of vector systems would therefore be of benefit.

Promoters which are suitable for the present invention may be any strong constitutive promoter which is capable of promoting expression of an associated coding DNA sequence in the liver. Such strong constitutive promoters include the human and murine cytomegalovirus [CMV] promoter, truncated CMV promoters, human serum albumin promoter [HAS] and α-1-antitrypsin promoter. In a specific embodiment, the promoter used is a truncated CMV promoter from which binding sites for known transcriptional repressors have been deleted.

The liver-specific enhancer elements useful for the present invention may be any liver-specific enhancer that is capable of enhancing tissue-specific expression of an associated coding DNA sequence in the liver. Such liver-specific enhancers include one or more human serum albumin enhancers, human prothrombin enhancers, α-1 microglobulin enhancers and an intronic aldolase enhancers. In preferred embodiments, multiple enhancer elements may be combined in order to achieve higher expression.

Among the preferred embodiments of the present invention are vectors comprising one or more HSA enhancers in combination with either a CMV promoter or an HSA promoter; one or more enhancer elements selected from the group consisting of the human prothrombin (HPrT) enhancer and the α-1microglobulin (A1MB) enhancer in combination with a CMV promoter; and one or more enhancer elements selected from the group consisting of HPrT enhancers and A1MB enhancers, in combination with an α-1-antitrypsin promoter.

Figure 1:
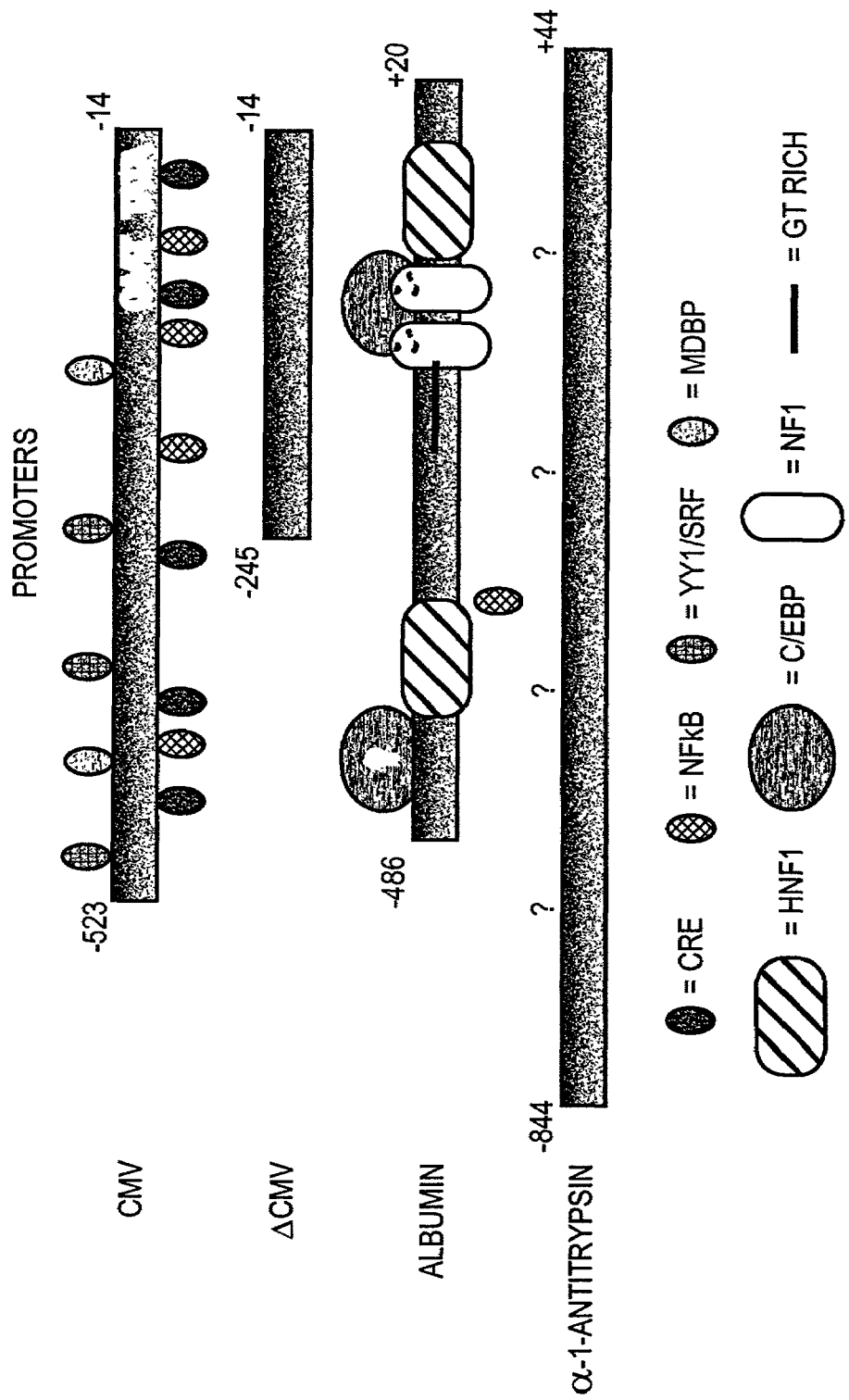
FIG. 1 is a depiction of the transcription factor binding sites present in the CMV, HSA and α-1 antitrypsin promoter regions.
Figure 2:
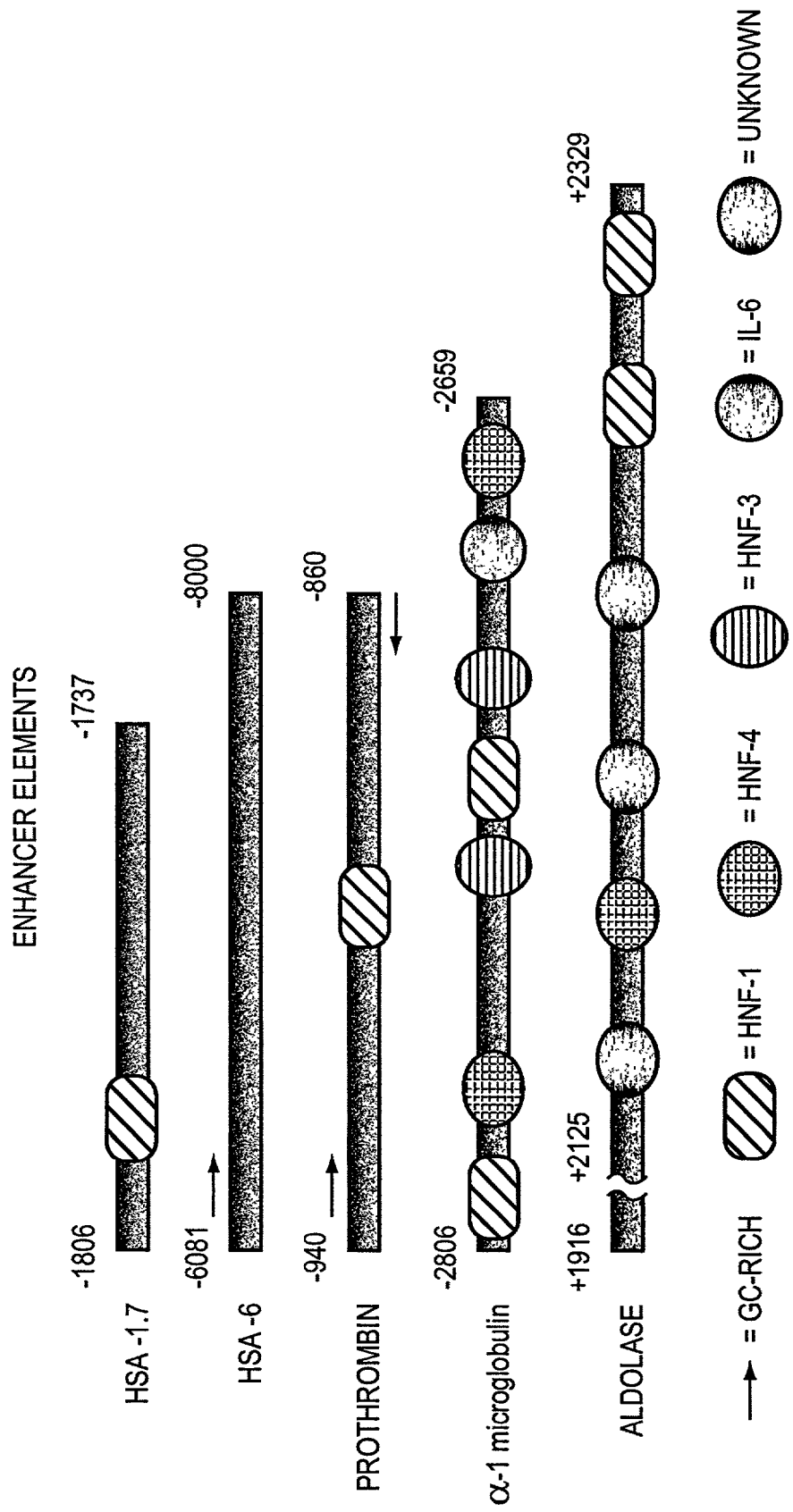
FIG. 2 is a depiction of the transcription factor binding sites present in the HSA enhancers (HSA-1.7, nucleotides −1806 to −1737; HSA-6, nucleotides −6081 to −6000), a human prothrombin enhancer (−940 to −860), an α-1microglobulin enhancer (−2806 to −2659) and an intronic aldolase enhancer (+1916 to +2329).
Figure 3:
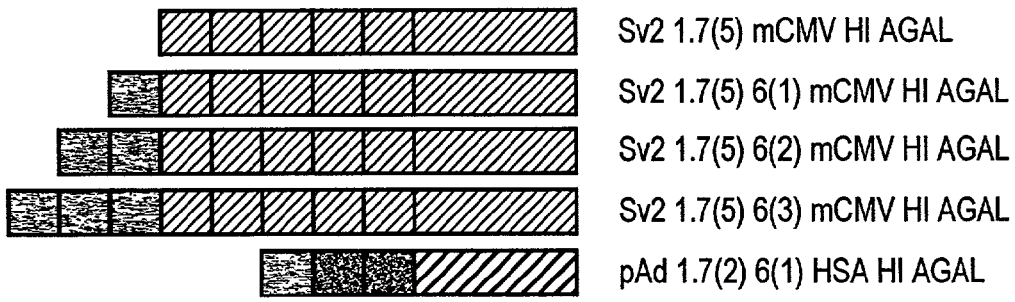
FIG. 3 is a schematic representation of an initial series of enhancer/promoter combinations. Group A indicates the combinations of the HSA enhancers that were linked to either the mCMV or HSA promoter. Groups B and C represent the combinations of either the human prothrombin (HPrT) or α-1microglobulin (A1MB) enhancer linked to the mCMV promoter. Groups D and E represent the combinations of of either HPrT or A1MB linked to the α-1-antitrypsin promoter.
Figure 3:
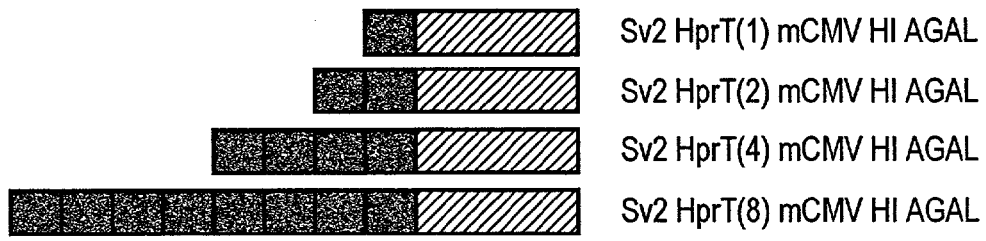
Figure 3:
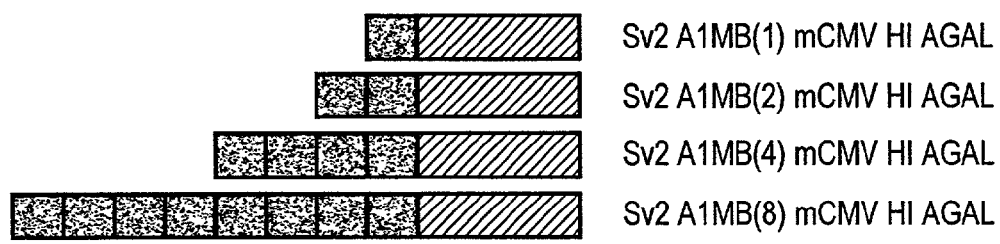
Figure 3:
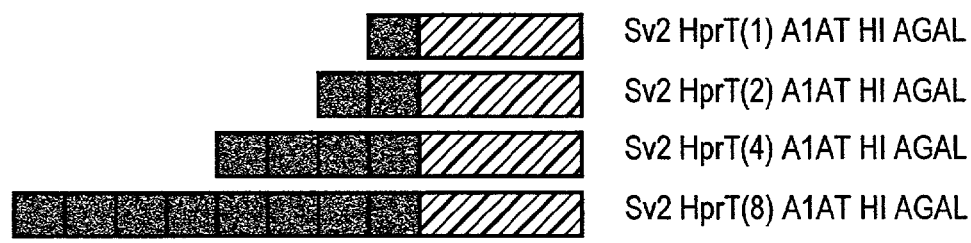
Figure 3:
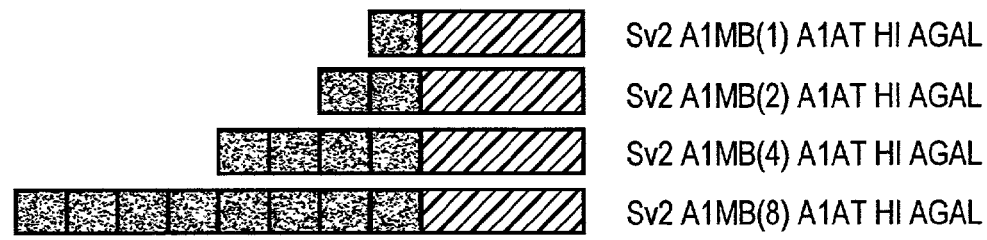

The strategy for achieving high and sustained levels of transgene expression involves combining promoter elements that have the potential to direct effective and sustained levels of expression with liver specific enhancer elements that can further increase expression. The promoter fragments preferred for use in the present invention include a truncated version of the CMV promoter (mCMV, nucleotides −245 to −14), human serum albumin promoter (−486 to +20) and α-1-antitrypsin promoter (−844 to −44). The truncated CMV promoter is missing binding sites for known transcriptional repressors and is thus a preferred version of this promoter. The human serum albumin and the α-1-antitrypsin promoter contain elements that direct basal yet liver specific expression. The transcription factor binding sites in these promoter regions are depicted in FIG. 1. The enhancer elements used here include two HSA enhancers (HSA-1.7, nucleotides −1806 to −1737; HSA-6, nucleotides −6081 to −6000), a human prothrombin enhancer (−940 to −860), an α-1microglobulin enhancer (−2806 to −2659) and an intronic aldolase enhancer (+1916 to +2329). Each of these enhancers has been shown to greatly increase transgene expression when linked to a minimal promoter and transcription factor binding sites in these enhancer elements is depicted in FIG. 2. FIG. 3 is a schematic representation of an initial series of enhancer/promoter combinations. Group A indicates the combinations of the HSA enhancers that were linked to either the mCMV or HSA promoter. Groups B and C represent the combinations of either the human prothrombin (HPrT) or α-1microglobulin (A1MB) enhancer linked to the mCMV promoter. Groups D and E represent the combinations of either HPrT or A1MB linked to the α-1-antitrypsin promoter.

Figure 4:
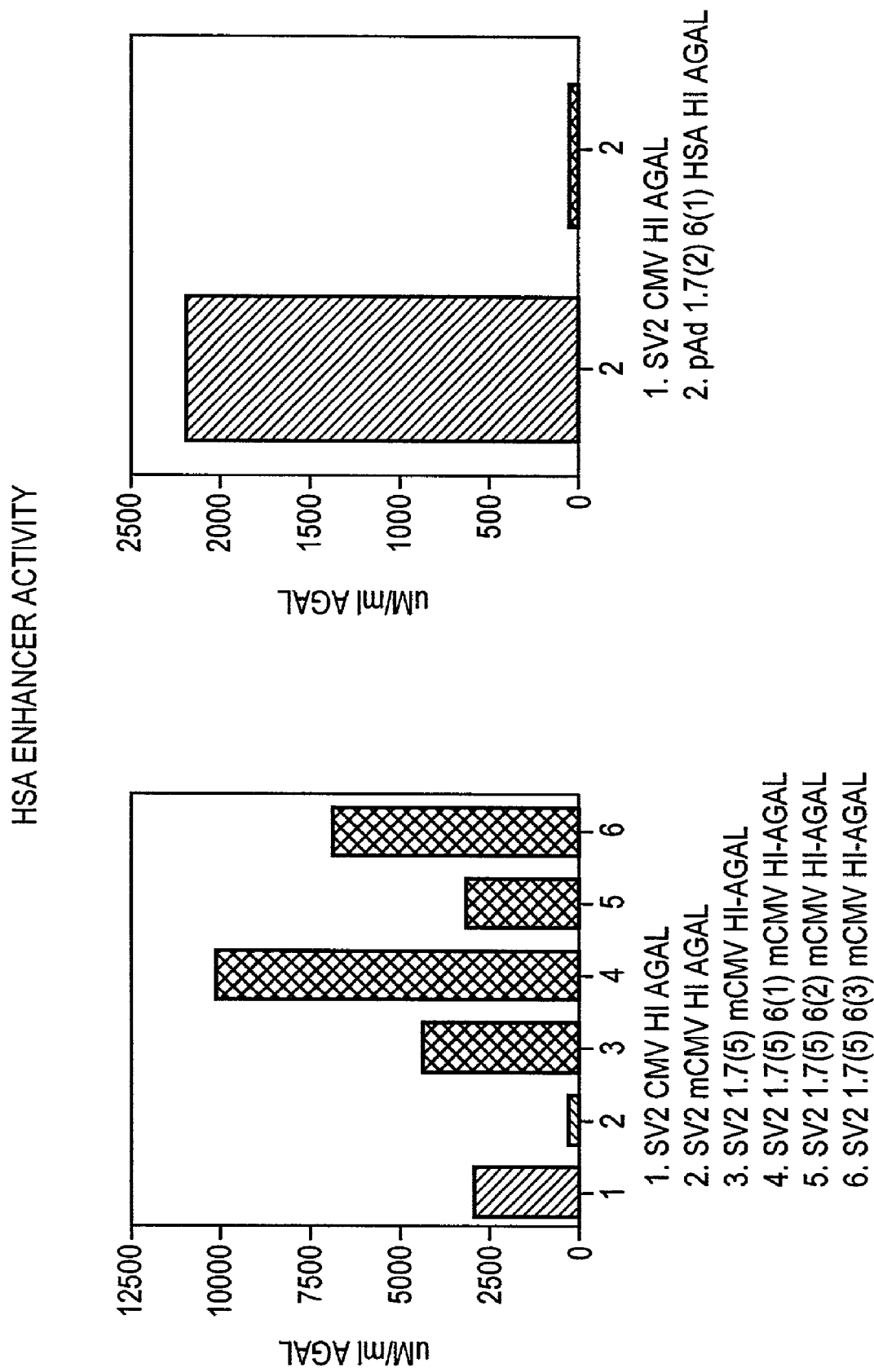
FIG. 4 depicts expression from mCMV promoter compared to that of hCMV promoter, and the effects of adding multiple HSA enhancers (HSA-1.7 and HSA-6).
Figure 5:
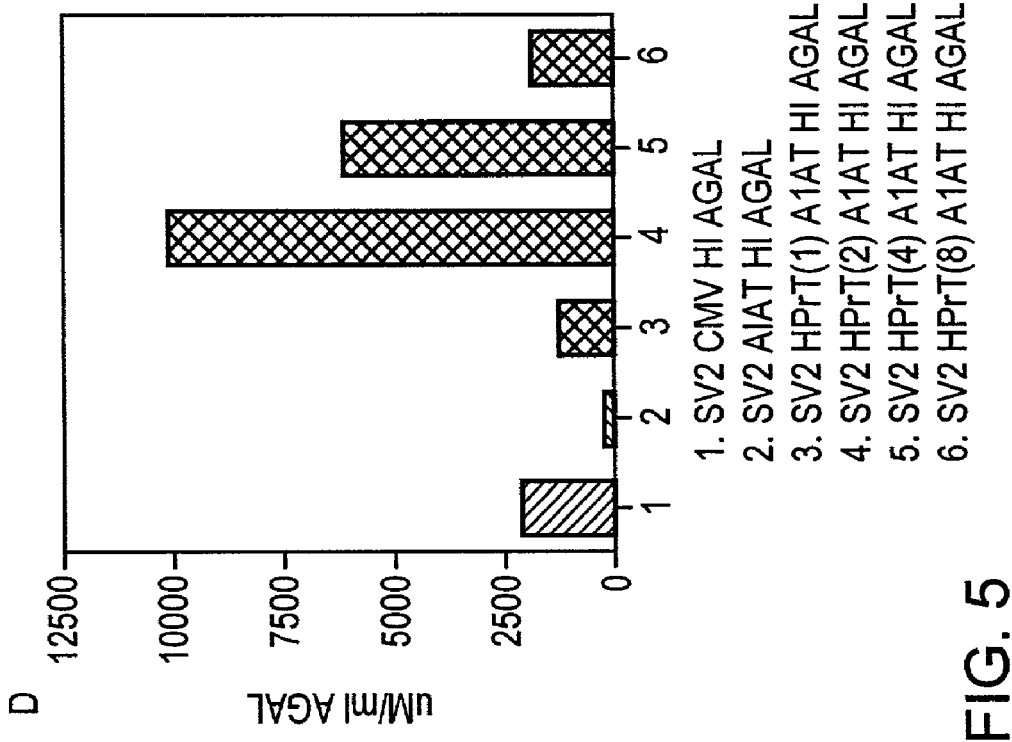
FIG. 5 depicts expression from constructs containing the HPrT enhancer. Linkage of this enhancer to the mCMV promoter (Panel B) elevated expression to near levels achieved with the CMV promoter but did not exceed it. Expression from the α-1-antitrypsin promoter was rather poor, however when two copies of the HPrT enhancer are added expression from this combination exceeds that from the CMV promoter.
Figure 5:
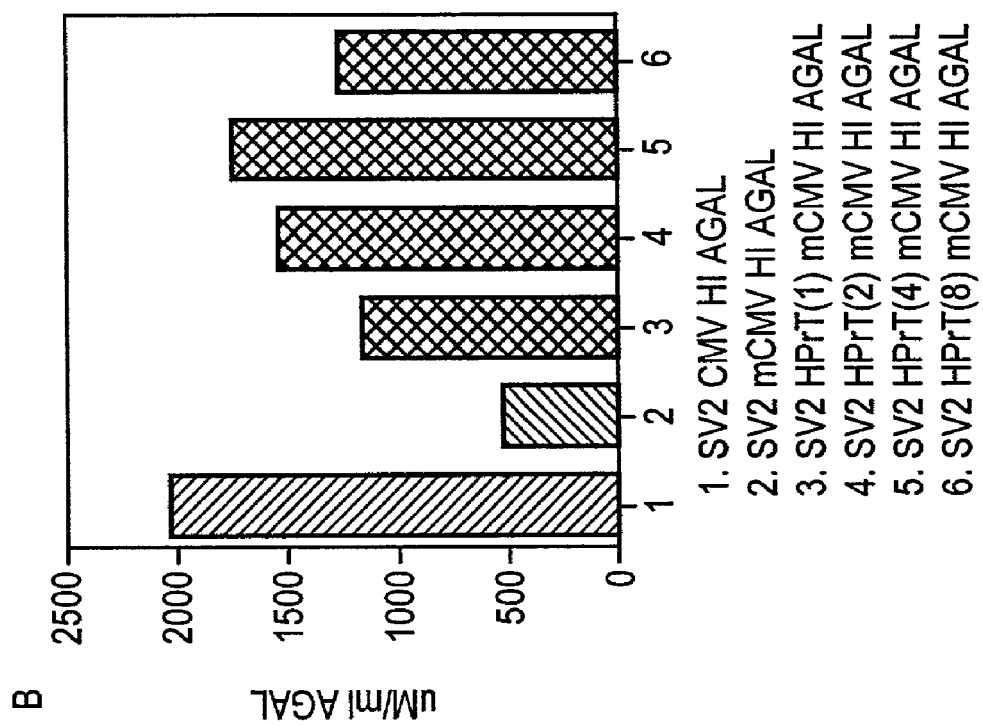
Figure 6:
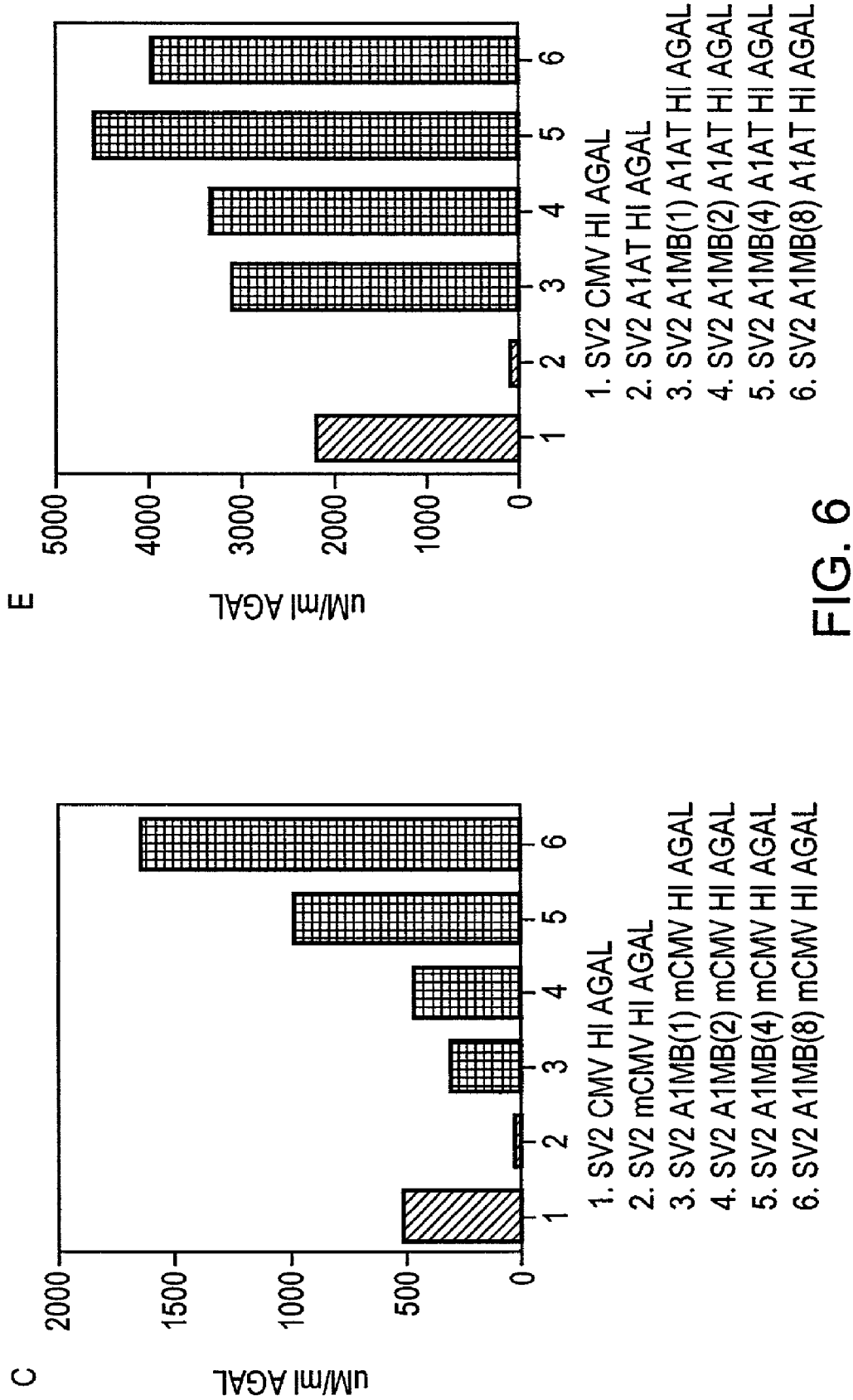
FIG. 6 depicts expression results from constructs containing the A1MB enhancer. Progressively increased expression is seen with increasing copy number of this enhancer (up to eight copies) linked to the mCMV promoter (Panel C). All copy combinations of this enhancer linked to the α-1-antitrypsin promoter yielded expression levels comparable to that obtained with the CMV promoter (Panel E).
Figure 7:
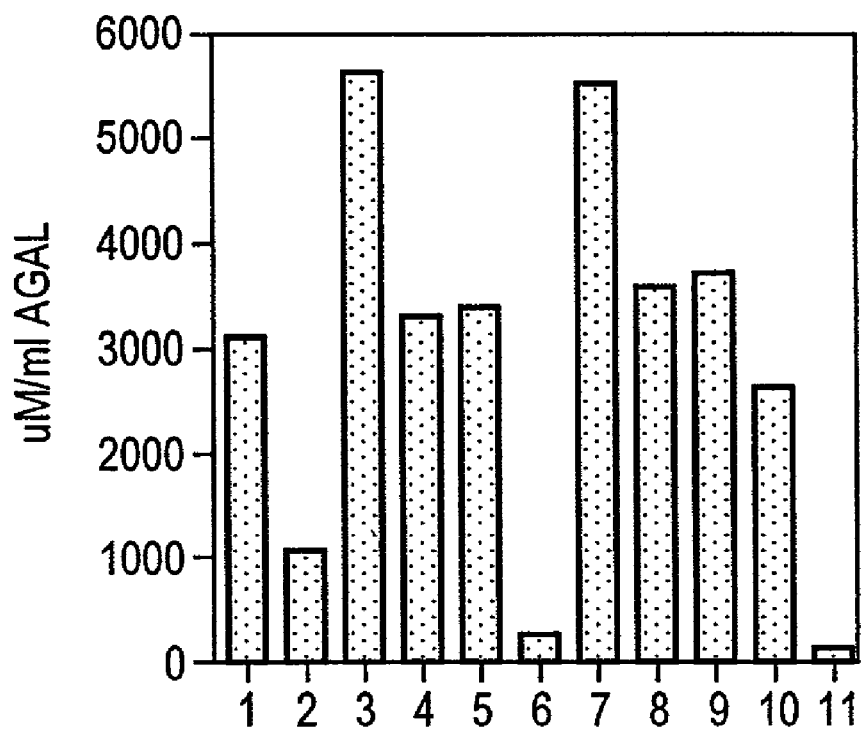
FIG. 7 depicts expression results obtained with representative candidates from each vector series that yielded equivalent or higher levels of α-galactosidase expression compared to the CMV promoter.
Figure 8:
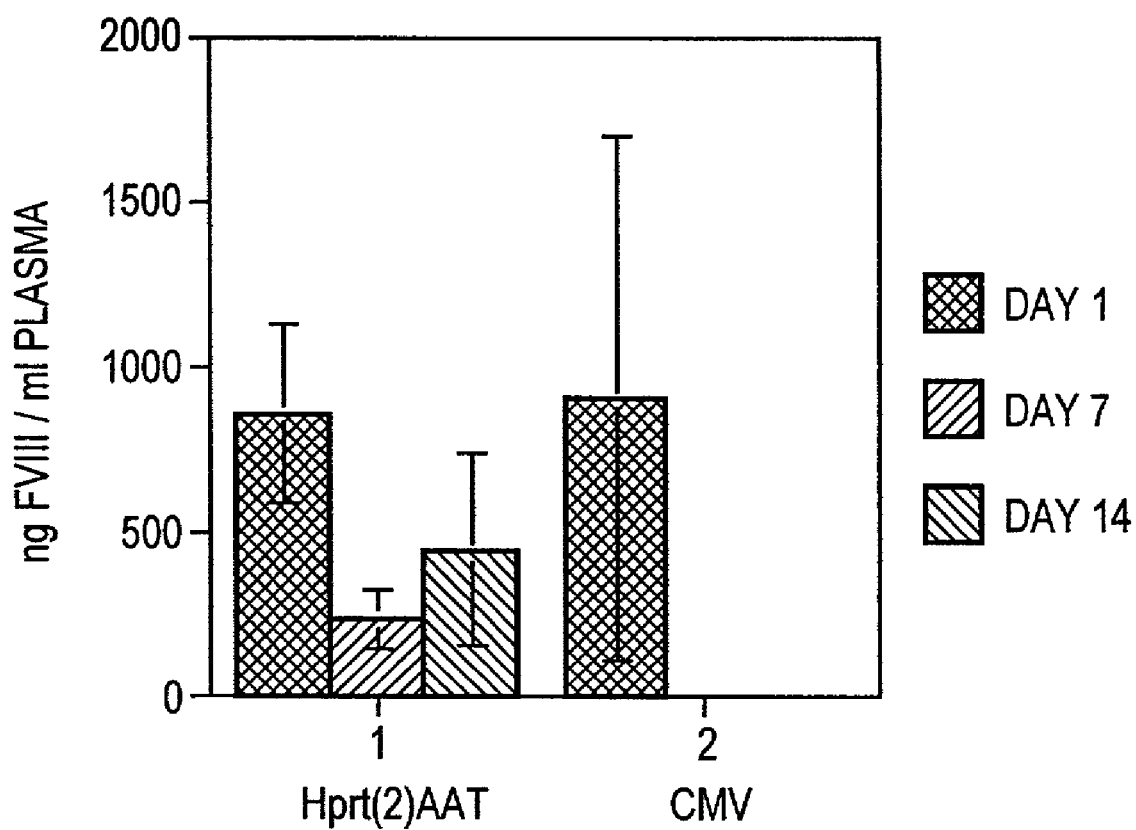
FIG. 8 demonstrates the expression of FVIII in SCID Beige Mice. The Factor VIII expression cassettes used contained either the CMV promoter or a hybrid promoter composed of two copies of the hprt enhancer linked to a human α-1-antitrypsin promoter fragment (Hprt(2)AAT). Ten μg of plasmid DNA containing either cassette was injected via the tail vein of SCID beige mice using Mirus plasmid delivery technology. Mice were bled at one, seven and fourteen days post-injection and FVIII levels in the plasma were determined by an ELISA that is specific for human FVIII. Each bar represents the average FVIII expression in the plasma of four mice.

Each of these enhancer/promoter combinations was linked to α-galactosidase and was tested for activity in Hep3B cells by measuring the levels of α-galactosidase in the supernatant medium following transient transfection. As shown in FIG. 4, expression from the mCMV promoter is reduced compared to the CMV promoter. However, the combination of five copies of the HSA-1.7 enhancer with one copy of the HSA-6 enhancer linked to the mCMV promoter yielded expression that was higher than that obtained with the CMV promoter. The expression results from constructs containing the HPrT enhancer are shown in FIG. 5. Linkage of this enhancer to the mCMV promoter (Panel B) elevated expression to near levels achieved with the CMV promoter but did not exceed it. Expression from the α-1-antitrypsin promoter was rather poor, however when two copies of the HPrT enhancer are added expression from this combination exceeds that from the CMV promoter. The expression results from constructs containing the A1MB enhancer are shown in FIG. 6. Progressively increased expression is seen with increasing copy number of this enhancer (up to eight copies) linked to the mCMV promoter (Panel C). All copy combinations of this enhancer linked to the α-1-antitrypsin promoter yielded expression levels comparable to that obtained with the CMV promoter (Panel E). Representative candidates from each vector series that yielded equivalent or higher levels of α-galactosidase expression compared to the CMV promoter were retested in a single experiment. As shown in FIG. 7, all enhancer/promoter combinations yielded comparable expression with expression from the HSA-1.7(5) HSA-6(1)mCMV and HPrT(2)A1AT promoters being the highest. These results demonstrate that high levels of expression are achievable by combining multiple copies of liver specific enhancers with various promoter elements.

EXAMPLES

1. Plasmid Constructions

The alpha one antitrypsin promoter (−1200 to +44) was PCR-amplified with Vent DNA polymerase (New England Bio Labs, Beverly, Mass. USA) from an in-house pBr 322 vector that contains a 19-kb genomic Sal I fragment which includes human PI derived from phage clone αNN (Dycaico et al. Science 242:1409-1412. 1988). The promoter was then cloned between the Hind III-EcoR I sites of pBluescript II SK+ (Stratagene, La Jolla, Calif. USA) to generate pBs A1AT. The sequence was analyzed using a PE Biosystems 377 automated sequencer. The hybrid alpha-galactosidase cassette from an in-house vector was cloned into the Spe I site of pBs A1AT to generate pBs A1AT HI AGAL. The alpha one antitrypsin hybrid intron alpha-galactosidase cassette was then subcloned into the pAdQuick (formerly pAdvantage) shuttle vector Sv2 ICEU I to generate Sv2 A1AT HI AGAL.

Human liver specific enhancer elements from albumin 60 bp and 81 bp; (1.7 kb and 6 kb from the transcription initiation site, respectively); prothrombin 81 bp (−940 to −860); and Alpha-1 microglobulin/Bikunin 154 bp (−2806 to −2653) were obtained via PCR from genomic DNA or through oligo synthesis. Multiple copies were cloned into Bluescript II SK+ (Stratagene, La Jolla Calif., USA). These enhancer elements were then subcloned into Sv2 A1AT HI AGAL via Cla 1-Stu 1, reducing the alpha one antitrypsin promoter to (−844 to +44) or subcloned into the in-house vector Sv2 CMV HI AGAL II via Cla 1-SnaB 1, truncating the wild-type cytomegalovirus promoter to (−245 to −14).

2. Hep3 B Transfections

Six well plates were seeded with Hep3 B cells at 2×10⁵ cells per well. Diluted 2.5 µg enhancer construct +2.5 ug CMV B (Stratagene, La Jolla, Calif. USA) in 1.5 mls opti-mem reduced serum media (Gibco BRL, Gaithersburg, Md. USA). Diluted 20 µl lipofectamine 2000 (Gibco BRL, Gaithersburg, Md. USA) in 1.5 mls opti-mem reduced serum media. The two solutions were mixed and then incubated at room temperature for 30 min. While complexes formed, cells were rinsed twice with opti-mem reduced serum media. Incubated cells with the lipid solution (1.5 mls solution per well) for 3-4 hrs at 37° c. in 5% co$_2$ incubator. Cells were rinsed once with 1×PBS and the lipid solution was replaced with 2 mls Mem media containing 1 mM Sodium pyruvate and 10% Fetal Bovine Serum. (Gibco BRL, Gaithersburg, Md. USA).

3. Alpha-galactosidase Fluorescent Assay

One hundred microliters of supernatant from hepatoma transfections were transferred into 96-well plate (Corning flat bottom). Five-fold dilutions were prepared to 1:125. Alpha-galactoside A enzyme (Genzyme, Framingham, Mass. USA) was diluted two fold 1250 uU/ml to 19.5 uU/ml to generate a standard curve. Substrate solution (1.69 mg/ml 4-methylumbelliferyl-a-D-galactoside and 26 mg/ml N-acetyl-D-galactosamine) in a buffer containing 27 mM citric acid, 46 mM sodium phosphate dibasic pH4.4 was added to the samples. Samples were incubated at 37° C. for 3 hours. The reactions were terminated with the addition of fifty microliters of a one molar sodium hydroxide solution. Spectra Max Gemini (Molecular Devices Co. Sunnyvale, Calif. USA) were read with excitation filter 365 nm and emission filter 450 nm. Alpha-galactosidase activity was normalized to α-galactosidase activity in transfection cell lysates using Galacto-light Plus kit. (Tropix, Bedford, Mass., USA). All α-galactosidase assay reagents were obtained from Sigma, St. Louis, Mo., USA.

The disclosures of all references disclosed herein are hereby incorporated by reference. The invention has been described in detail with particular reference to preferred embodiments thereof. However, it is contemplated that modifications and improvements within the spirit and teachings of this invention may be made by those in the art upon considering the present disclosure. Such modifications and improvements constitute part of the present claimed invention.

The invention claimed is:

1. A recombinant DNA vector, comprising a human serum albumin promoter and two human prothrombin enhancers.

2. The recombinant DNA vector according to claim 1, further comprising a coding DNA sequence operatively linked to said promoter and enhancers.

3. A recombinant DNA vector, comprising an α-1-antitrypsin promoter and two human prothrombin enhancers.

4. The recombinant DNA vector according to claim 3, further comprising a coding DNA sequence operatively linked to said promoter and enhancers.

5. A recombinant DNA vector, comprising an α-1-antitrypsin promoter and two α-1 microglobulin (A1MB) enhancers.

6. The recombinant DNA vector according to claim 5, further comprising a coding DNA sequence operatively linked to said promoter and enhancers.

7. A recombinant adenoviral vector comprising the recombinant DNA vector of claims 1, 3, or 5.

8. The recombinant adenoviral vector of claim 7 wherein said recombinant DNA vector further comprises a coding DNA sequence operatively linked to said promoter and enhancers.

9. A recombinant adeno-associated viral vector comprising the recombinant DNA vector of claims 1, 3, or 5.

10. The adeno-associated viral vector of claim 9 wherein said recombinant DNA vector further comprises a coding DNA sequence operatively linked to said promoter and enhancers.

11. The recombinant DNA vector according to any one of claims 2-6, wherein the coding DNA sequence is alpha-galactosidase.

* * * * *